United States Patent
Pistner

(10) Patent No.: US 9,389,138 B2
(45) Date of Patent: Jul. 12, 2016

(54) APPARATUS AND METHOD TO DETECT DAMAGE OF A COMPONENT OF A SYSTEM

(71) Applicant: General Electric Company, Schenectady, NY (US)

(72) Inventor: Alexander James Pistner, Atlanta, GA (US)

(73) Assignee: General Electric Company, Schenectady, NY (US)

( * ) Notice: Subject to any disclaimer, the term of this patent is extended or adjusted under 35 U.S.C. 154(b) by 800 days.

(21) Appl. No.: 13/661,447

(22) Filed: Oct. 26, 2012

(65) Prior Publication Data

US 2014/0121995 A1    May 1, 2014

(51) Int. Cl.
| | |
|---|---|
| *G01B 21/32* | (2006.01) |
| *G06F 19/00* | (2011.01) |
| *G01M 5/00* | (2006.01) |
| *G01N 27/20* | (2006.01) |
| *G01B 7/16* | (2006.01) |

(52) U.S. Cl.
CPC .............. *G01M 5/0016* (2013.01); *G01B 7/18* (2013.01); *G01M 5/0033* (2013.01); *G01M 5/0083* (2013.01); *G01N 27/205* (2013.01)

(58) Field of Classification Search
CPC ............. G01B 7/16; G01B 7/18; G01M 5/00; G01M 5/0016; G01M 5/0083; G01M 5/0033; G01N 27/20; G01N 27/202; G01N 27/205; F01D 21/00; G06F 19/00
See application file for complete search history.

(56) References Cited

U.S. PATENT DOCUMENTS

| | | | |
|---|---|---|---|
| 4,896,537 A | 1/1990 | Osborne | |
| 6,499,350 B1 | 12/2002 | Board et al. | |
| 7,298,152 B1 | 11/2007 | Wilke et al. | |
| 7,469,595 B2 | 12/2008 | Kessler et al. | |
| 7,725,269 B2 | 5/2010 | Kessler et al. | |
| 7,966,578 B2 | 6/2011 | Tolmasky et al. | |
| 2005/0284232 A1* | 12/2005 | Rice | 73/762 |
| 2006/0132149 A1* | 6/2006 | Twerdochlib | 324/693 |
| 2006/0254366 A1* | 11/2006 | Williamson et al. | 73/786 |
| 2009/0044595 A1* | 2/2009 | Vokey | 73/1.17 |
| 2009/0192727 A1* | 7/2009 | Ford | 702/33 |
| 2011/0107843 A1* | 5/2011 | Hucker et al. | 73/802 |

(Continued)

FOREIGN PATENT DOCUMENTS

GB    2405934 A    3/2005

OTHER PUBLICATIONS

Ciang et al., Structural health monitoring for a wind turbine system: a review of damage detection methods, Oct. 13, 2008, Measuremnt Science and Technology, p. 1-20.*

(Continued)

*Primary Examiner* — John Breene
*Assistant Examiner* — Mohammad Islam
(74) *Attorney, Agent, or Firm* — Fletcher Yoder, P.C.

(57) ABSTRACT

An apparatus and method detect damage of a component of a system. The damage detection apparatus includes a first grid of sensors arranged in a first orientation on a surface of the component and configured to generate a first set of signals. The apparatus also includes a second grid of sensors, independent from the first grid of sensors, arranged in a second orientation on an insulating layer on the surface of the component and configured to generate a second set of signals, the second orientation overlapping with the first orientation. A processor detects the damage based on a change in at least one signal of the first set of signals or the second set of signals.

20 Claims, 2 Drawing Sheets

(56) References Cited

U.S. PATENT DOCUMENTS

2012/0188078 A1 7/2012 Soles et al.
2012/0318925 A1* 12/2012 Gibson et al. .............. 244/158.3

OTHER PUBLICATIONS

EP Search Report and Written Opinion dated Mar. 4, 2014 issued in connection with corresponding EP Patent Application No. 13189118.6.

* cited by examiner

APPARATUS AND METHOD TO DETECT DAMAGE OF A COMPONENT OF A SYSTEM

BACKGROUND OF THE INVENTION

The subject matter disclosed herein relates to component characterization and, more specifically, to damage detection.

The ability to detect deformation or liberation of a component of a system can mitigate collateral damage to other parts of the system. For example, in a gas turbine, stator vanes, shaped as an airfoil, for example, are used to control the pressure and velocity of airflow. When one or more of the vanes (blades) experiences a deformation on its surface or liberation from the remaining set of stator vanes, the collateral effect of the damage to that vane is a degradation in the gas turbine performance and reliability.

In prior systems, any damage to a component, such as the stator vane in the example above, was detected based on downstream effects, such as a change in the vibration signature or temperature in the gas turbine example. However, when deformation or liberation is detected based on downstream effects, the overall system has already suffered ill effects. Further, not every deformation may require immediate corrective action. For example, based on the location of a deformation, a required repair may be imminent but not immediate, thereby allowing a delay in system shutdown to perform the repair. Thus, timely and accurate identification of a deformation or liberation of a system component, such as an airfoil, would be appreciated.

BRIEF DESCRIPTION OF THE INVENTION

According to one aspect, a damage detection apparatus to detect damage of a component of a system includes a first grid of sensors arranged in a first orientation on a surface of the component and configured to generate a first set of signals; a second grid of sensors, independent from the first grid of sensors, arranged in a second orientation on the surface of the component and configured to generate a second set of signals, the second orientation overlapping with the first orientation; and a processor configured to detect the damage based on a change in at least one signal of the first set of signals or the second set of signals.

According to another aspect, a method of detecting damage of a component of a system includes disposing a first grid of sensors in a first orientation on a surface of the component, the first grid of sensors configured to generate a first set of signals; disposing a second grid of sensors, independent from the first grid of sensors, in a second orientation on the surface of the component, the second orientation overlapping with the first orientation, and the second grid of sensors configured to generate a second set of signals; and processing the first set of signals and the second set of signals to detect the damage based on a change in at least one signal of the first set of signals or the second set of signals.

These and other advantages and features will become more apparent from the following description taken in conjunction with the drawings.

BRIEF DESCRIPTION OF DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 2:
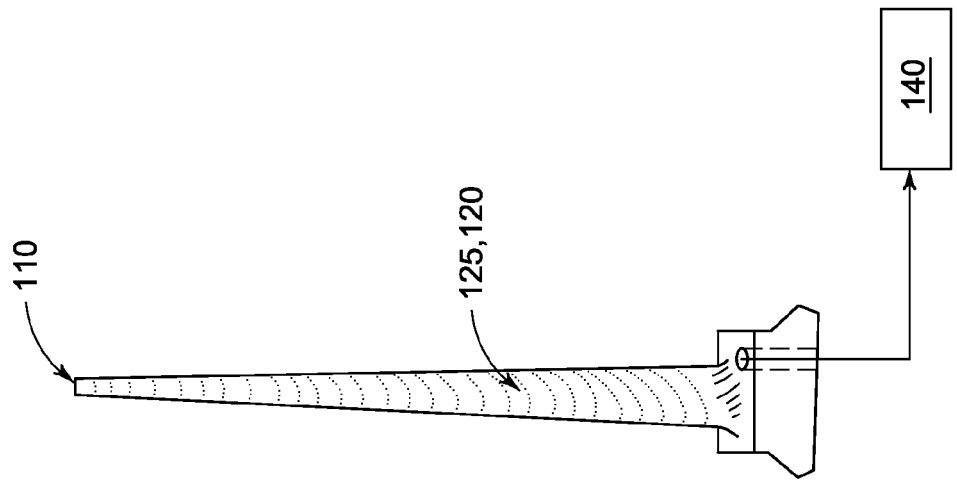
FIG. 2 depicts a perspective side view of the airfoil integrated with the damage detection system according to the embodiment of FIG. 1.
Figure 1:
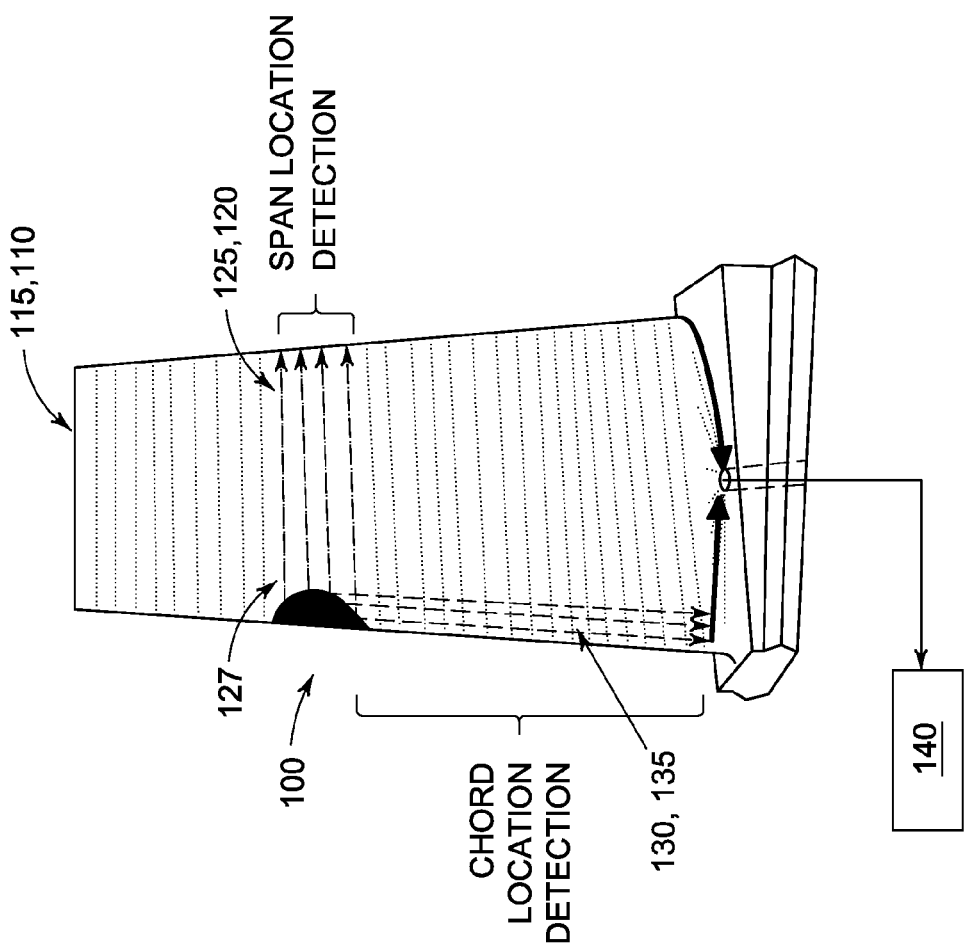
FIG. 1 depicts a perspective front view of an airfoil integrated with a damage detection system according to an embodiment.

FIGS. 1 and 2 depict perspective front and side views, respectively, of a component 110 integrated with a damage detection system 100 according to an embodiment. The exemplary component 110 shown in FIGS. 1 and 2 is an airfoil 115. However, the damage detection system 100 may be used to detect damage to any component 110 of any system. When the component 110 is a rotating component, the damage detection system 100 includes a slip ring. The damage detection system 100 includes a set of sensors 120 arranged in one direction (shown as horizontal in FIG. 1) on the surface of the component 110 and a set of sensors 130 arranged in another direction (shown as vertical in FIG. 1), as well as a processor 140. Although the sensors 120 and 130 are shown as being perpendicular in FIG. 1, the two sets of sensors 120 and 130 need only have overlapping orientations but not necessarily perpendicular orientations. The two sets of sensors 120 and 130 may be, for example, grids of current-carrying wires 125 and 135. Each of the grids of current-carrying wires 125 and 135 is independent. That is, an insulating layer 127 separates the two sets of sensors 120, 130. Thus, while the orientations of the grids of current-carrying wires 125 and 135 overlap, the grid of current-carrying wires 125 is not disposed to intersect with or touch the grid of current-carrying wires 135 initially.

The processor 140 senses the signal on each sensor 120 and 130 and detects damage to the component 110 based on a change in at least one of the signals. In alternate embodiments, a signal need not be continuously present at both sensors 120, 130. In this case, a change a signal indicating a change in status based on interference between the two sets of sensors 120, 130 is used.

The processor 140 functionality is detailed with reference to the exemplary embodiment of the component 110 being an airfoil 115 and the sensors 120 and 130 being grids of current-carrying wires 125 and 135. When a part of the airfoil 115 is deformed, the current-carrying wire 125 oriented in one direction (horizontal in FIG. 1) at the area of deformation touches a current-carrying wire 135 oriented in the other direction (vertical in FIG. 1) which is also at the area of deformation, resulting in a short circuit at the area of the deformation. This short circuit results from the insulating layer 127 being breached due to the deformation. As noted above with regard to the alternate embodiments, only one of the sets of current-carrying wires 125, 135 needs to be driven (actively carrying current) for the short circuit to occur. The processor 140, which initially detects the expected current flow through one set or both sets of the active current-carrying wires 125 and 135, detects the overcurrent in one or more sets of the current-carrying wires 125 and 135. The deformation that caused the short circuit may, therefore, be localized based on which set or sets of current-carrying wires 125 and 135 exhibit the overcurrent condition. In various embodiments, the processor 140 may be a network of two or more processors 140 and may work in conjunction with one or more memory devices. The processor 140 may include a current detector and various control functions and may be implemented in a computer, with a microcontroller, a microprocessor, or other programmable computing device.

When a part of the airfoil 115 is liberated (broken off), the current carrying wires 125 and 135 associated with that area of the airfoil 115 are broken, as well. This results in an open circuit at the break and a loss of current flow. The processor 140, which initially detects the expected current flow through one set or both sets of the active current-carrying wires 125 and 135, detects the loss of signal or lack of current flow in one or more of the current-carrying wires 125 and 135. The liberation that caused the open circuit may, therefore, be localized based on which current-carrying wires 125 and 135 exhibit the loss of signal. The reference to active current-carrying wires 125 and 135 above is meant to indicate that all the current-carrying wires 125 and 135 need not actively carry current at all times. That is, based on a given operating condition, only certain portions of the component 110 (e.g., airfoil 115) may be under stress or of concern on a continual basis. Alternately, only a periodic check of the entire surface may be needed to ensure that deformation or liberation has not occurred since the last check. When continuous monitoring of the entire surface of the component 110 is not needed, only current-carrying wires 125 and 135 in the regions of interest or all current-carrying wires 125 and 135 at periods of interest may be driven with current.

Figure 3:
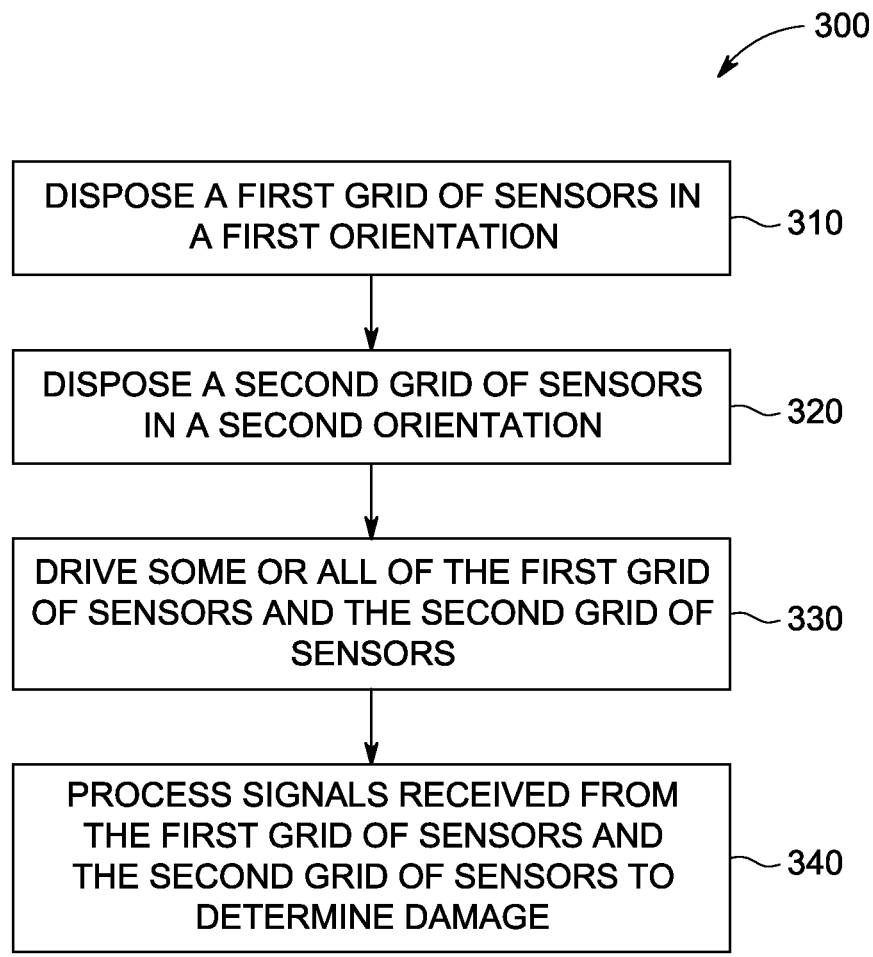
FIG. 3 depicts the processes involved in damage detection of a component according to an embodiment.

FIG. 3 depicts the processes 300 involved in damage detection of a component 110 according to an embodiment. The processes 300 include disposing a first grid of sensors 120 in a first orientation at block 310. At block 320, disposing a second grid of sensors 130 in a second orientation includes the second orientation overlapping the first orientation but not necessarily being perpendicular with the first orientation. Disposing the second grid of sensors 130 at block 320 also includes maintaining the second grid of sensors 130 separate from the first grid of sensors 120 to ensure that they do not touch or intersect. The processes 300 include driving some or all of the first grid of sensors 120 and the second grid of sensors 130 at block 330. Block 330 also includes periodically, rather than continuously, driving some or all of the sensors 120 and 130. As discussed above, only the current-carrying wires 125 and 135 in an area of an airfoil 115 may be driven based on the stresses experienced by the airfoil 115 in a given situation, for example. At block 340, processing signals received from the first grid of sensors 125 and the second grid of sensors 130 enables the processor 140 to determine a type and extent of damage to the component 110. For example, if only one current-carrying wire 125 from the first grid of sensors 120 and one current-carrying wire 135 from the second grid of sensors 130 exhibit an overcurrent due to a short circuit, the processor identifies a localized deformation of the airfoil 110. On the other hand, if the processor 140 stops receiving signals from several current-carrying wires 125 from the first grid of sensors 120 and several current-carrying wires 135 from the second grid of sensors 130, then the processor would identify a large portion of the airfoil 115 as being liberated from the turbine system.

By indicating the location and extent of damage to a component 110, the processor 140 facilitates analysis of the severity of its effect on the overall system. This analysis may then be used to determine whether and when a repair or replacement is needed. Without the information regarding a general location for the deformation, for example, the analysis of its severity on system functionality cannot be made, and a choice would have to be made whether to ignore all detected deformations until an effect is manifested in the overall system (e.g., gas turbine) or to repair all deformation. The first approach would be tantamount to the current state of damage analysis without a damage detection system 100. On the other hand, making repairs for every detected deformation may prove to be an inefficient approach, because the system would be shut down, possibly unnecessarily. With the information provided by the processor 140 using the damage detection system 100, more efficient damage handling is possible. For example, while an initially detected deformation may be determined not to necessitate a repair, the spread of that deformation may indicate that a repair is imminent.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. An apparatus to detect damage of a component of a system, the apparatus comprising:
a first grid of sensors arranged in a first orientation on a surface of the component and configured to generate a first set of signals when activated;
a second grid of sensors, independent from the first grid of sensors, arranged in a second orientation on an insulating layer on the surface of the component and configured to generate a second set of signals when activated, the second orientation overlapping with the first orientation; and
a processor configured to detect the damage based on a change in at least one signal of the first set of signals or the second set of signals, wherein the processor is configured to identify a plurality of types of the damage including a deformation and a liberation of a portion of the component that breaks off from the component based on the change in the at least one signal of the first set of signals or the second set of signals.

2. The apparatus according to claim 1, wherein the first orientation is perpendicular to the second orientation.

3. The apparatus according to claim 1, wherein the first grid of sensors is a first grid of current-carrying wires, and the second gird of sensors is a second grid of current-carrying wires.

4. The apparatus according to claim 3, wherein the processor is configured to identify the damage as the deformation when the change in the at least one signal is a change from an expected current value to an overcurrent.

5. The apparatus according to claim 4, wherein the processor is configured to estimate a shape and location of the deformation based on which one or more current-carrying wires of the first grid of current-carrying wires or the second grid of current-carrying wires exhibits the change and the overcurrent.

6. The apparatus according to claim 3, wherein the processor is configured to identify the damage as the liberation of the portion of the component when the change in the at least one signal is a change from an expected current value to no current flow.

7. The apparatus according to claim 6, wherein the processor is configured to estimate an extent and location of the liberation based on which one or more current-carrying wires of the first grid of current-carrying wires or the second grid of current-carrying wires exhibits the change.

8. The apparatus of claim of claim 3, wherein the processor is configured to determine a size of the damage based on which one or more current-carrying wires of the first grid of current-carrying wires or the second grid of current-carrying wires exhibits the change and to determine a degree of the damage based on the size of the damage.

9. The apparatus of claim 3, wherein the processor is configured to determine a location and a size of the damage based on which one or more current-carrying wires of the first grid of current-carrying wires or the second grid of current-carrying wires exhibits the change.

10. The apparatus of claim 9, wherein the processor is configured to determine a severity of an effect of the damage on the system based on the location and the size of the damage.

11. The apparatus of claim 10, wherein the processor is configured to determine whether to repair or replace the component based on the severity of the effect of the damage on the system.

12. The apparatus of claim 1, wherein the component comprises a blade, and the system comprises a turbine system.

13. The apparatus of claim 12, wherein the first grid of sensors and the second grid of sensors extend to a tip of the blade.

14. A method to detect damage of a component of a system, the method comprising:
  disposing a first grid of sensors in a first orientation on a surface of the component, the first grid of sensors configured to generate a first set of signals when activated;
  disposing a second grid of sensors, independent from the first grid of sensors, in a second orientation on an insulating layer on the surface of the component, the second orientation overlapping with the first orientation, and the second grid of sensors configured to generate a second set of signals when activated;
  processing the first set of signals and the second set of signals to detect the damage based on a change in at least one signal of the first set of signals or the second set of signals; and
  identifying a plurality of types of the damage including a deformation and a liberation of a portion of the component that breaks off from the component based on the change in the at least one signal of the first set of signals or the second set of signals.

15. The method according to claim 14, further comprising initiating current flow through one or more of the first grid of sensors or one or more of the second grid of sensors, the first grid of sensors being a first grid of current-carrying wires and the second grid of sensors being a second grid of current-carrying wires.

16. The method according to claim 15, wherein the processing includes detecting the change in the at least one signal as a change from an expected current value to an overcurrent, and wherein identifying the damage includes identifying the damage as the deformation based on the overcurrent.

17. The method according to claim 16, wherein the processing includes estimating a shape and location of the deformation based on which one or more current-carrying wires of the first grid of current-carrying wires or the second grid of current-carrying wires exhibits the change and the overcurrent.

18. The method according to claim 15, wherein the processing includes detecting the change in the at least one signal as a change from an expected current value to no current flow, and wherein identifying the damage includes identifying the damage as the liberation of the portion of the component based on the change from an expected current value to no current flow.

19. The method according to claim 18, wherein the processing includes estimating an extent and location of the liberation based on which one or more current-carrying wires of the first grid of current-carrying wires or the second grid of current-carrying wires exhibits the change.

20. The method of claim 15, comprising:
  determining a size of the damage based on which one or more current-carrying wires of the first grid of current-carrying wires or the second grid of current-carrying wires exhibits the change; and
  determining a degree of the damage based on the size of the damage.

* * * * *